(12) United States Patent
Bernard et al.

(10) Patent No.: US 6,777,575 B2
(45) Date of Patent: Aug. 17, 2004

(54) PROCESS FOR THE PREPARATION OF 2-ALKYLTHIO BENZOIC ACID DERIVATIVES

(75) Inventors: Didier Bernard, Lyons (FR); Agnès Viauvy, Saint Andeol Le Chateau (FR)

(73) Assignee: Rhone-Poulenc Agro, Lyons (FR)

( * ) Notice: Subject to any disclaimer, the term of this patent is extended or adjusted under 35 U.S.C. 154(b) by 214 days.

(21) Appl. No.: 09/462,181

(22) Filed: Mar. 28, 2000

(65) Prior Publication Data

US 2002/0103396 A1 Aug. 1, 2002

(30) Foreign Application Priority Data

Jul. 7, 1997 (GB) ............................................. 9714302

(51) Int. Cl.⁷ ............................................. C07C 321/00
(52) U.S. Cl. ......................................... 562/432; 560/18
(58) Field of Search ............................. 562/432; 560/18

(56) References Cited

U.S. PATENT DOCUMENTS

| | | | |
|---|---|---|---|
| 3,714,179 A | 1/1973 | Tweit | |
| 5,079,381 A | 1/1992 | Gregory et al. | |
| 5,092,919 A | 3/1992 | Nguyen | |
| 5,744,021 A | 4/1998 | Brungs et al. | |

FOREIGN PATENT DOCUMENTS

| | | |
|---|---|---|
| EP | 0418175 | 3/1991 |
| EP | 0527036 | 2/1993 |
| EP | 0560482 | 9/1993 |
| EP | 0780371 | 6/1997 |
| GB | 1453885 | 10/1976 |
| HU | 208 309 B | 9/1993 |
| WO | 95/31446 | 11/1995 |

OTHER PUBLICATIONS

Beck et al, *J. Org. Chem*, vol. 43, No. 10, pp. 2052–2055 (1978).

Ruff et al, *Tetrahedron*, vol. 34, pp. 2767–2773 (1978).

Baldwin, *Journal of Medicinal Chemistry*, vol. 30, No. 3, Mar. 1987, pp. 690–695, XP002085482.

Patent Abstracts of Japan, JP5–8198464A, abstract of JP 57082062, published Nov. 18, 1983.

*Primary Examiner*—Paul J. Killos
(74) *Attorney, Agent, or Firm*—Burns, Doane, Swecker & Mathis, L.L.P.

(57) ABSTRACT

A process for preparing a compound of the formula

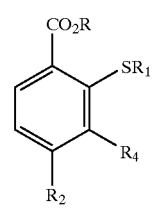

(I)

comprising reacting a compound of the formula

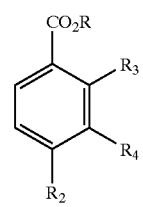

(II)

wherein $R_3$ is nitro or halo, or a salt thereof, with a compound of the formula $R_1SX$ (III) wherein X is hydrogen or alkali metal.

6 Claims, No Drawings

PROCESS FOR THE PREPARATION OF 2-ALKYLTHIO BENZOIC ACID DERIVATIVES

This application is a national stage filing under 35 U.S.C. § 371 of International Application No. PCT/EP98/04946 filed on Jul. 3, 1998, which International Application was published by the International Bureau in English on Jan. 21, 1999.

This invention relates to a process for preparing certain 2-alkylthio substituted benzoic acid derivatives and their salts and esters, which are useful as intermediates in the preparation of herbicidally active compounds.

European Patent Publication No. 527036 discloses 2-methylthio-4-trifluoromethylbenzoic acid and a preparation for it. However the method described employs organolithium reagents at low temperatures which are unsuitable for large scale preparations.

The reaction to prepare 4-alkylthiosubstituted benzoate esters by the reaction of 4-halo-benzoate esters with alkyl mercaptans is known, for example as described in U.S. Pat. Nos. 1,453,885 and 5,092,919. The corresponding reaction to prepare 4-alkiylthio substituted benzoic acids by the reaction of 4-chlorobenzoic acids with alkyl mercaptans is also known, for example as reported by Beck and Yahner in J. Org. Chem. 43(10), 2052 (1978), Japanese Patent J5 8198-464 and UK Patent No. 1,453,885.

Reactions to prepare 2-alkylthio-substituted benzoic acid esters are also known for example as described in EP0560482 and WO9531446. EP0780371 also discloses the preparation of 2-alkylthio-4-trifluoromethylbenzoic acid esters. However, to the applicants knowledge there are only two references which report the displacement of a 2-halo group by alkyl mercaptans to give 2-alkylthio substituted benzoic acids, and neither of these reactions is performed using the benzoic acid as reactant. Thus F.Ruff et al. in Tetrahedron Volume 34, 2767 (1978) describes the preparation of 2-methylthio-5-nitrobenzoic acid by the reaction of methyl mercaptan with methyl 2-chloro-5-nitrobenzoate in the presence of base. In this case the 2-chlorine atom is very highly activated by the presence of the 5-nitro group. The second reference U.S. Pat. No. 3,714,179 illustrates the difficulty of displacement of the 2-fluorine atom in ethyl 2-fluorobenzoate, with the product ethyl 2-methylthiobenzoate being obtained after heating for a 3 week period.

It is desirable to provide intermediates which are used in multi-step synthetic sequences in high yields and also to develop new procedures which allow the efficient displacement of 2-halo or 2-nitro-substituted benzoic acids and their salts and esters to furnish 2-alkylthio substituted benzoic acids and their salts and esters.

It is therefore an object of this invention to provide a process for preparing 2-alkylthio substituted benzoic acids and their salts and esters proceeding in high yield, and requiring a short reaction period. The present invention allows this object to be met in whole or in part.

Thus, the present invention provides a process for the preparation of a compound of formula (I):

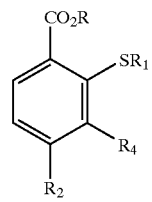

(I)

wherein R represents hydrogen, or $C_{1-6}$ alkyl;
$R_1$ represents $C_{1-6}$ alkyl;
$R_2$ represents $C_{1-6}$ haloalkyl, $C_{1-6}$ alkyl, $C_{1-6}$ haloalkoxy, $C_{1-6}$ alkoxy, $SO_nR_5$ or halogen;
$R_4$ represents hydrogen, $C_{1-6}$ haloalkoxy, $C_{1-6}$ alkoxy, $SO_nR_5$ or halogen; or a 5 or 6-membered heterocyclic ring (which may be unsaturated or partially saturated) containing 1 to 3 hetero atoms selected from oxygen, nitrogen and sulphur, optionally substituted by halogen, $C_{1-6}$ haloalkyl, $C_{1-6}$ alkyl, $C_{1-6}$ haloalkoxy, $C_{1-6}$ alkoxy, $SO_nR_5$, nitro or cyano;
$R_5$ represents $C_{1-6}$ alkyl; and
n represents 0, 1 or 2;
or a salt thereof: which process comprises the reaction of a compound of formula (II):

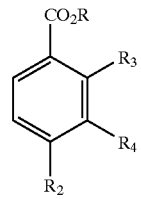

(II)

wherein R, $R_2$ and $R_4$ are as hereinbefore defined, and $R_3$ represents nitro or a halogen atom selected from fluorine, chlorine and bromine; or a salt thereof, with a compound of formula (III):

$R_1SX$      (III)

wherein $R_1$ is as hereinbefore defined, and X represents hydrogen or an alkali metal.

When $R_4$ represents a heterocyclic ring, preferred rings include 3-isoxazolyl, 5-isoxazolyl, 2-thiazolyl, 5-oxazolyl, 2-furyl, 3-furyl, 2-thienyl and 3-thienyl.

R preferably represents hydrogen, methyl or ethyl.
$R_1$ preferably represents methyl.
$R_2$ preferably represents trifluoromethyl.
$R_3$ preferably represents fluorine or chlorine.
$R_4$ preferably represents hydrogen.
X preferably represents hydrogen or a sodium, potassium or lithium atom.

When salts are used in the above reaction, preferably the salts are alkali metal salts.

In an especially preferred embodiment of the invention $R_1$ represents $C_{1-6}$ alkyl (methyl is most preferred);
$R_2$ represents $C_{1-6}$ haloalkyl (trifluoromethyl is most preferred);
$R_3$ represents a halogen atom selected from fluorine, chlorine and bromine (fluorine or chlorine are most preferred); and $R_4$ represents hydrogen.

Generally the reaction of a compound of formula (II) with a compound of formula (III) is performed under substantially anhydrous conditions. It has been found that the reaction proceeds in excellent yield under such conditions.

Generally the reaction takes place with less than about 5% by volume water content, preferably less than about 2%, even more preferably less than about 1%, typically from about 0.005 to about 0.05%. It will however be understood that in certain cases slightly more or less water may be tolerated, depending on the nature of the solvents used and the temperature of the reaction, the compound of formula (I) or salt thereof to be prepared and other reaction conditions.

The reaction may be carried out using a number of solvents, but is preferably performed in a polar aprotic solvent for example N,N-dimethylformamide, N,N-dimethylacetamide, N-methylpyrrolidinone, acetonitrile or dimethylsulphoxide. Preferred solvents are N-methylpyrrolidinone, acetonitrile or dimethylsulphoxide, the former two being preferred when the process is performed on a large scale, for reasons of cost and availability.

Where X is hydrogen. a base is preferably also present in the reaction mixture. Examples of suitable bases are alkali metal carbonates, alkoxides or hydrides such as potassium carbonate, potassium t-butoxide or sodium hydride. or amidine bases such as 1,8-diazabicyclo[5.4.0]undec-7-ene or 1.1.3.3-tetramethylguanidine.

The reaction is generally performed at a temperature from −20° C. to 150° C. For compounds of formula (II) wherein R represents hydrogen or an alkali metal, a temperature of from about 50° C. to about 100° C. is preferred. For compounds of formula (II) wherein R represents $C_{1-6}$ alkyl, a temperature of from about 0° C. to about 50° C. is preferred.

The molar ratio of the benzoic acid derivative of formula (II): alkyl thiol of formula (III) is generally from about 1:1 to about 1:2. preferably from about 1:1 to about 1:1.5, even more preferably from about 1:1.05 to about 1:1.3.

In one embodiment of the above reaction to prepare compounds of formula (I) from compounds of formula (II). R represents hydrogen or the compound of formula (II) is used in the form of a salt, preferably an alkali metal salt.

Compounds of formula (II) and (III) above are known in the literature or can be prepared using known methods.

The following non-limiting examples illustrate the invention.

EXAMPLE 1

Preparation of 2-methylthio-4-trifluoromethylbenzoic Acid

A mixture of anhydrous sodium thiomethoxide (0.39 g, 0.00525M), 2-chloro-4-trifluoromethylbenzoic acid sodium salt (1.23 g, 0.005M) and anhydrous N-methylpyrrolidinone (10 ml, containing less than 0.01% of water) was heated at 90° C. for 2 hours. The mixture was cooled to 20° C., acidified and extracted (t-butyl methyl ether). The extract was washed (water) and evaporated to give 2-methylthio-4-trifluoromethylbenzoic acid (1.18 g, 100% yield). $^1$H-nmr 2.40(s,3H). 7.30(1H), 7.38(1H), 8.07(1H). The purity of the product was greater than 95%.

By proceeding as described above but using dimethylsulphoxide instead of N-methylpyrrolidinone there was obtained 2-chloro-4-trifluoromethylbenzoic acid in 99% yield (purity>95%).

By proceeding as described above but using a 9:1 mixture of acetonitrile and N-methylpyrrolidinone instead of N-methylpyrrolidinone alone, there was obtained 2-chloro-4-trifluoromethylbenzoic acid in 97% yield (purity greater than 95%).

EXAMPLE 2

The effect of the presence of water in the reaction mixture was analysed in the following experiment. The conditions of Example 1 were repeated at 100° C. but using 1.3 equivalents of sodium thiomethoxide and N-methylpyrrolidinone as solvent containing the percentages of water (by volume) shown in Table 1.

TABLE 1

| % Water | Temperature | % Yield |
|---------|-------------|---------|
| 20      | 100° C.     | 12      |
| 1       | 80° C.      | 79      |
| 0.01    | 90° C.      | 100     |

The above results indicate that increasing concentrations of water leads to a decreasing yield of product.

EXAMPLE 3

The effect of temperature was examined by repeating the conditions of Example 1 at various temperatures. Table 2 shows the results for two sets of reactions, one set where 0.01% water was present and the other where 2% water was present:

TABLE 2

| 2% Water    |       | Anhydrous (0.01% water) |       |
|-------------|-------|-------------------------|-------|
| Temperature | Yield | Temperature             | Yield |
| 60° C.      | 3%    | 80                      | 91%   |
| 80° C.      | 52%   | 90                      | 100%  |
| 100° C.     | 65%   | −(1)                    | −(1)  |

Note (1): this experiment was not performed.

EXAMPLE 4

Dry sodium thiomethoxide (0.385 g. 0.0055M) was added to a stirred solution of methyl 2-chloro-4-trifluoromethylbenzoate (1.19 g, 0.005M) in anhydrous N-methylpyrrolidinone (10 ml) at 5° C. The mixture was acidified and extracted (t-butyl methyl ether), washed (water) and evaporated to give methyl 2-methylthio-4-trifluoromethylbenzoate (1.18 g, 94% yield). $^1$H-nmr 2.44 (s,3H). 3.89(s,3H). 7.33(1H), 7.41(1H), 8.02(1H).

By proceeding in a similar manner but using ethyl 2-chloro-4-trifluoromethylbenzoate there was prepared:

ethyl 2-methylthio-4-trifluoromethylbenzoate, $^1$H-nmr 1.34(t,3H), 2.42(s,3H), 4.34(q,2H), 7.32(1H), 7.40 (1H), 8.02(1H), obtained in 95% yield.

The above experiments therefore clearly demonstrate the advantage of the process of the invention over the prior art, thereby providing access to valuable intermediates in higher yield and shorter reaction period.

The compounds obtained by the process of the present invention may be used in the preparation of herbicidally active compounds as described, for example, in European Patent Publication Nos. 0418175, 0527036 and 0560482.

What is claimed is:

1. A process for the preparation of a compound of formula (I):

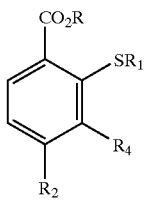

(I)

wherein R represents hydrogen or $C_{1-6}$ alkyl;

$R_1$ represents $C_{1-6}$ alkyl;

$R_2$ represents $C_{1-6}$ haloalkyl, $C_{1-6}$ alkyl, $C_{1-6}$ haloalkoxy, $C_{1-6}$ alkoxy, $SO_nR_5$ or halogen;

$R_4$ represents hydrogen, $C_{1-6}$ haloalkoxy, $C_{1-6}$ alkoxy, $SO_nR_5$ or halogen; or a 5 or 6-membered heterocyclic ring which may be unsaturated or partially saturated having 1 to 3 hetereo atoms selected from oxygen, nitrogen and sulphur, optionally substituted by halogen, $C_{1-6}$ haloalkyl, $C_{1-6}$ alkyl, $C_{1-6}$ haloalkoxy, $C_{1-6}$ alkoxy $SO_nR_5$, nitro or cyano;

$R_5$ represents $C_{1-6}$ alkyl; and n represents 0, 1 or 2;

or a salt thereof; which process comprises reacting a compound of formula (II):

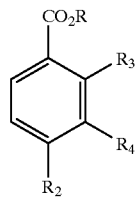

(II)

wherein R, $R_2$ and $R_4$ are as hereinbefore defined, and $R_3$ represents nitro or a halogen atom selected from fluorine, chlorine and bromine; or a salt thereof, with a compound of formula (III):

$R_1SX$ (III)

wherein $R_1$ is as hereinbefore defined, and X represents hydrogen or an alkali metal;

wherein the water content in the reaction mixture is less than 5 % by volume;

wherein the process is performed under substantially anhydrous conditions; and wherein the process is carried out using at least one solvent selected from the group consisting of N-methylpyrrolidinone, acetonitrile, dimethyl-sulphoxide and combinations thereof.

2. A process according to claim 1 which is performed in an aprotic solvent.

3. A process according to claim 1 in which the molar ratio of the benzoic acid derivative of formula (II): alkyl thiol of formula (III) is from 1:1 to 1:2.

4. A process according to claim 1 in which $R_1$ represents $C_{1-6}$ alkyl, $R_2$ represents $C_{1-6}$ haloalkyl and $R_4$ represents hydrogen.

5. A process according to claim 1 in which $R_1$ represents methyl, $R_2$ represents trifluoromethyl and $R_4$ represents hydrogen.

6. A process according to claim 1 in which R represents hydrogen.

* * * * *